United States Patent [19]

Rahtz et al.

[11] 4,011,322

[45] Mar. 8, 1977

[54] BENZIMIDAZOLE DERIVATIVES AND PROCESS FOR THE PRODUCTION THEREOF

[75] Inventors: Dieter Rahtz; Hans Wendt; Henning Koch, all of Berlin, Germany

[73] Assignee: Schering Aktiengesellschaft, Berlin & Bergkamen, Germany

[22] Filed: July 28, 1975

[21] Appl. No.: 599,398

[30] Foreign Application Priority Data

July 29, 1974 Germany .................. 2436883

[52] U.S. Cl. .................. 424/250; 260/268 BC
[51] Int. Cl.² .................. C07D 403/06
[58] Field of Search .............. 260/268 BC; 424/250

[56] References Cited

UNITED STATES PATENTS 3,658,822    4/1972    Fauran et al. ............... 260/268 BC Primary Examiner—Donald G. Daus
Assistant Examiner—Jose Tovar
Attorney, Agent, or Firm—Millen & White

[57] ABSTRACT

Benzimidazoles of the formula

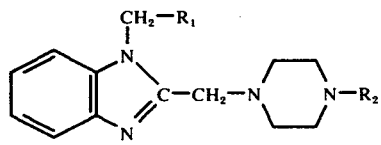

wherein $R_1$ is o-hydroxyphenyl, a p-chlorophenyl, or p-fluorophenyl, and $R_2$ is an alkyl of 2–4 carbon atoms, and physiologically acceptable acid addition salts thereof possess topical anti-inflammatory activity.

8 Claims, No Drawings

BENZIMIDAZOLE DERIVATIVES AND PROCESS FOR THE PRODUCTION THEREOF

BACKGROUND OF THE INVENTION

This invention relates to novel, pharmacologically active benzimidazole derivatives.

SUMMARY OF THE INVENTION

In a composition aspect, this invention relates to novel benzimidazole derivatives of the general Formula I

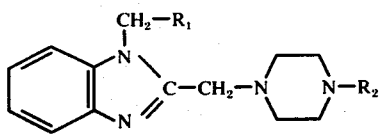

wherein $R_1$ is o-hydroxyphenyl, a p-chlorophenyl, or p-fluorophenyl, and $R_2$ is an alkyl of 2–4 carbon atoms, and physiologically acceptable acid addition salts thereof.

In another composition aspect, this invention relates to pharmaceutical compositions comprising a benzimidazole derivative of this invention in admixture with a pharmaceutically acceptable carrier.

In process aspects, this invention relates to methods for the production and use of the novel benzimidazoles of this invention.

DETAILED DISCUSSION

The $R_2$ alkyl group can be a straight-chain or branched, viz., ethyl, propyl, isopropyl, butyl, isobutyl, sec.-butyl and tert.-butyl. Preferred $R_2$ alkyl groups are straight-chain.

In a process aspect, this invention relates to a process for the preparation of the novel benzimidazole derivatives and physiologically acceptable acid addition salts thereof in which, in a conventional manner:

a. a compound of general Formula II

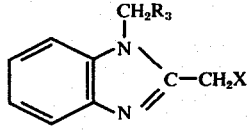

wherein $R_3$ is o-hydroxyphenyl, o-acyloxyphenyl, o-benzyloxyphenyl, p-chlorophenyl, or p-fluorophenyl, and X is a halogen atom, alkylsulfonyloxy or arylsulfonyloxy, is condensed with an N-alkyl piperazine of general Formula III

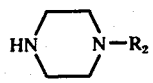

wherein $R_2$ has the values given above; or b. a compound of general Formula IV

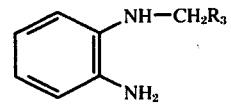

wherein $R_3$ has the values given above, is condensed with a piperazine derivative of general Formula V

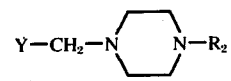

wherein $R_2$ has the values given above and Y is carboxyl, alkoxycarbonyl, a chlorocarbonyl, or alkyl formimido; or c. a compound of general Formula VI

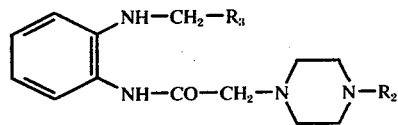

wherein $R_2$ and $R_3$ have the values given above, is cyclized; or d. a compound of general Formula VII

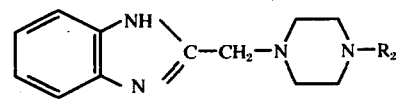

wherein $R_2$ has the values given above, is condensed with a compound of general Formula VIII $$X-CH_2R_3 \qquad \text{VIII}$$

wherein $R_3$ and X have the values given above; and, thereafter, an acyloxy group or benzyloxy group optionally present on the $R_3$ group is split off, and, if desired, the thus-obtained benzimidazole derivative of general Formula I is converted with acid into a physiologically acceptable acid addition salt thereof.

If the process of this invention is carried out using starting compounds of general Formulae II, IV, VI, or VIII which contain as the substituent $R_3$ as an o-acyloxyphenyl group, preferably the acyloxy group contains 2–8 carbon atoms. Suitable acyloxy groups are, for example, alkanoyloxy groups, e.g., acetoxy, propionyloxy, and trimethylacetoxy group, and benzoyloxy.

If the process is conducted using starting compounds of general Formula II or VIII wherein X is alkylsulfonyloxy or arylsulfonyloxy, X is preferably methanesulfonyl or p-toluenesulfonyl.

If the process is carried out using starting compounds of general Formula V wherein the Y is alkoxycarbonyl or alkyl formimido, the alkyl residue in Y is preferably a lower alkyl of 1–4 carbon atoms.

The process of this invention is, as already mentioned, an analogous process. This process can be conducted, for example, using the conditions described in German Unexamined Laid-Open Application DOS No. 1,470,319.

The novel benzimidazole derivatives of general Formula I can be converted in a manner known per se into the water-soluble acid addition salts thereof with physiologically acceptable acids. Suitable acids are, for example, mineral acids, such as sulfuric acid, phosphoric acid, or hydrochloric acid, or organic dicarboxylic acids or tricarboxylic acids, such as oxalic acid, succinic acid, malonic acid, maleic acid, malic acid, dl-tartaric acid, or citric acid.

The novel benzimidazole derivatives of general Formula I are pharmacologically active and are distinguished especially upon topical application by strong anti-inflammatory activity, particularly in the case of dermatoses of inflammatory origin. They differ in this respect from known benzimidazole derivatives which, upon topical administration, are inactive or have a substantially weaker activity (U.S. Pat. No. 3,423,413).

The anti-inflammatory effectiveness of the novel benzimidazole derivatives can be determined in the conventional vasoconstriction test, as follows:

On the backs of volunteers for the experiment, the stratum corneum was removed by the application and tearing off of an adhesive strip, applied 20 times at the same spot, thus producing a pronounced hyperemia. Within the stripped area, respectively 50 mg. of ointment was applied to marked areas having a size of 4 cm$^2$, this ointment containing respectively 0.1, 0.01 or 0.001%, respectively, of the compound to be tested or of the reference substance in a water-oil base. One, two, three, and four hours after application, the extent of vasoconstriction was determined.

To determine the vasoconstriction, which is a representative syndrome of topical anti-inflammatory activity, the color value of the untreated skin and the treated stripped skin is measured and compared with the color value of the normal skin, with the color value of the normal skin being assigned the value 100 and the color value of the untreated stripped skin being assigned the value 0. Minor, medium, and high-grade vasoconstriction are evaluated with values between 0 and 100.

The results of such tests employing compounds of this invention (Compounds III and IV) and the prior art compounds Clemizole (I) and Flucortolone (II) are shown in Table I below.

TABLE I

| | VASOCONSTRICTION TEST: | | | | |
|---|---|---|---|---|---|
| | | Effective Agent Concentration | Observation Time in Hours | | |
| No. | Compound | % | 1 | 4 | 8 |
| I | 1-4'Chlorobenzyl-2-pyrrolidinomethyl-benzimidazole (= Clemizole) | 0.1 | 18 | 35 | 45 |
| | | 0.01 | 18 | 31 | 33 |
| II | 6 α-Fluoro-11β,21-dihydroxy-16α-methyl-1,4-pregnadiene-3,20-dione (= Fluocortolone) | 0.1 | 35 | 75 | 85 |
| | | 0.01 | 15 | 65 | 85 |
| | | 0.001 | 20 | 50 | 60 |
| III | 2-(4-Ethyl-1-piperazinyl)-methyl-1-(2-hydroxybenzyl)-benzimidazole | 0.1 | 45 | 80 | 85 |
| | | 0.01 | 35 | 55 | 55 |
| | | 0.001 | 15 | 15 | 20 |
| IV | 2-(4-Ethyl-1-piperazinyl)-methyl-1-(4-chlorobenzyl)-benzimidazole | 0.01 | 30 | 85 | 100 |
| | | 0.001 | 25 | 65 | 95 |

The anti-inflammatory activity of the novel benzimidazole derivatives upon local application can also be determined in accordance with the method by Tonelli, as follows:

The compound to be tested is dissolved in an irritant, consisting of 4 parts of pyridine, 1 part of distilled water, 5 parts of ether, and 10 parts of a 4% ether croton oil solution. Felt strips attached to the insides of a slide tweezer are saturated with this test solution, and the tweezers with the felt strips were pressed under slight pressure for 15 seconds against the right ear of male rats weighing 100–160 g.

The left ear remains untreated and serves as comparison. Three hours after application, the animals are sacrificed and disks having a size of 9 mm. are punched out of their ears. The weight difference between the disk of the right ear and that of the left ear is a measure for the thus-produced edema.

Control animals are treated in the same way, with the difference that the irritant solution employed does not contain any test substance.

The concentration of active agent ($ED_{50}$) is determined which, when used, results in a 50% reduction of the edema formation.

The results of tests involving a compound of this invention (Compound V) and the prior art compounds Clemizole (I) and Fluorocortolone (II) is shown in Table II below.

TABLE II

| No. | EDEMA TEST: Compound | $ED_{50}$ |
|---|---|---|
| I | "Clemizole" | 8.8 |
| II | "Fluocortolone" | 3.4 |
| V | 2-(4-Propyl-1-piperazinyl)-methyl-1-(4-fluorobenzyl)-benzimidazole | 3.1 |

It can be seen from the tables that the novel benzimidazole derivatives are distinguished from conventional compounds of analogous structure by superior anti-inflammatory activity. The anti-inflammatory effectiveness of the novel benzimidazole derivatives is, upon local application, approximately as strong as that of conventional corticoids having anti-inflammatory effects.

The corticoids used heretofore for the treatment of skin inflammations exhibit a systemic effect in addition to the topical effect. These corticoids can enter the bloodstream even upon topical administration, due to resorption through the inflamed skin or due to skin injuries, where they affect the body functions in a great variety of ways in their capacity of hormone-active substances. This disadvantage does not exist in the topically effective benzimidazole derivatives of the present invention. Moreover, the benzimidazole derivatives have the advantage of low toxicity.

The novel compounds are suitable in combination with the vehicles customary in galenic pharmacy, for the local treatment of allergies, contact dermatitis, eczema of a great variety of types, neurodermatitis, erythrodermia, burns, pruritis vulvae et ani, rosacea, erythematodes cutaneus, psoriasis, lichen ruber planus et verrucosus, and similar skin diseases.

The pharmaceutical compositions are prepared in the usual manner by converting the effective agents with suitable additives into the desired topical form of application, e.g., solutions, lotions, ointments, creams, inhalants, or plasters. In the thus-formulated medicinal agents, the concentration of active agent is dependent on the form of administration. In case of lotions and ointments, preferably an effective agent concentration of 0.005 to 5% is employed.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1 a. Under agitation, 73.3 g. of salicylaldehyde is added dropwise under ice cooling gradually to a solution of 6.4 g. of o-phenylenediamine in 225 ml. of methanol and 0.6 ml. of piperidine. The mixture is allowed to stand for one hour; the thus-separated precipitate is vacuum-filtered, washed twice with ice-cold methanol, and 112 g. of N-(2-hydroxybenzal)-o-phenylenediamine is obtained as a crude product.

b. 106 g. of N-(2-hydroxybenzal)-o-phenylenediamine (crude product) is dissolved in 1,300 ml. of dioxane, combined with 11 g. of Raney nickel, and hydrogenated at 70° C. under an initial pressure of 120 atmospheres hydrogen pressure. The catalyst is then removed by filtration, the filtrate is concentrated under vacuum, and the residue is mixed with ether. The thus-separated product is vacuum-filtered, washed with ether, and the yield is 83 g. of N-(2-hydroxybenzyl)-o-phenylenediamine as a crude product.

c. 77.5 g. of the thus-obtained N-(2-hydroxybenzyl)-o-phenylenediamine (crude product) is introduced in incremental portions under agitation and cooling with ice water into a suspension of 59 g. of chloroacetic acid imino ether hydrochloride in 500 ml. of chloroform. Then, the mixture is stirred for 30 minutes at room temperature and another 2 hours at 40° C. The precipitate is vacuum-filtered, washed with chloroform and water, and dried, thus obtaining 95 g. of 2-chloromethyl-1-(2-hydroxybenzyl)-benzimidazole as the crude product.

d. A mixture of 5.5 g. of the thus-produced 2-chloromethyl-1-(2-hydroxybenzyl)-benzimidazole (crude product), 2.5 g. of N-ethylpiperazine, and 1.1 g. of sodium carbonate in 50 ml. of 95% ethanol is refluxed for 4 hours. The mixture is then introduced into 150 ml. of ice water, the precipitate is vacuum-filtered, washed with water, dried, and recrystallized from isopropyl alcohol, yielding 5.5 g. of 2-(4-ethyl-1-piperazinyl)-methyl-1-(2-hydroxybenzyl)-benzimidazole, m.p. 249° C.

EXAMPLE 2

Under agitation, 21.9 g. of N-ethylpiperazine (98% strength), dissolved in 30 ml. of absolute benzene, is added dropwise to a solution of 23.9 g. of 1-(4-chlorobenzyl)-2-(chloromethyl)-benzyl-imidazole in 165 ml. of absolute benzene. The mixture is then allowed to stand for 16 hours at room temperature and thereafter heated for 2 hours under reflux. The thus-obtained mixture is filtered; the filtrate is washed, dried, and concentrated under vacuum.

The residue is taken up in 1N hydrochloric acid, washed with methylene chloride, and aqueous phase is decolorized with carbon and rendered alkaline with sodium hydroxide solution. The mixture is then extracted with methylene chloride, the methylene chloride phase is concentrated under vacuum, the thus-obtained residue is purified by chromatography over a silica gel column with the use of methanol-chloroform as the eluents, and the product is recrystallized from hexane, thus obtaining 19 g. of 2-(4-ethyl-1-piperazinyl)-methyl-1-(4-chlorobenzyl)-benzimidazole, m.p. 134°–135° C.

EXAMPLE 3

Under the conditions of Example 2, it is possible to react 1-(4-fluorobenzyl)-2-chloromethyl-benzimidazole with N-propylmorpholine to obtain 2-(4-propyl-1-piperazinyl)-methyl-1-(4-fluorobenzyl)-benzimidazole, m.p. 108° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A benzimidazole derivative of the formula

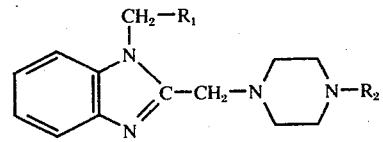

wherein $R_1$ is o-hydroxyphenyl, p-chlorophenyl, or p-fluorophenyl, and $R_2$ is an alkyl of 2–4 carbon atoms, or a physiologically acceptable acid addition salt thereof.

2. A compound of claim 1, wherein $R_2$ is ethyl.
3. A compound of claim 1 wherein $R_2$ is n-propyl.
4. A compound of claim 1, 2-(4-ethyl-1-piperazinyl)-methyl-1-(2-hydroxybenzyl)-benzimidazole or a physiologically acceptable acid addition salt thereof.
5. A compound of claim 1, 2-(4-propyl-1-piperazinyl)-methyl-1-(4-fluorobenzyl)-benzimidazole or a physiologically acceptable acid addition salt thereof.
6. A compound of claim 1, 2-(4-ethyl-1-piperazinyl)-methyl-1-(4-chlorobenzyl)-benzimidazole or a physiologically acceptable acid addition salt thereof.
7. A pharmaceutical composition adapted for topical administration consisting essentially of an anti-inflammatorily effective concentration of a compound of claim 1 in admixture with a pharmaceutically acceptable carrier.
8. A method for the treatment of inflammations of the skin which consists essentially of applying to the affected area an anti-inflammatorily effective amount of a compound of claim 1.

* * * * *